United States Patent [19]

Boothe et al.

[11] Patent Number: 5,065,939
[45] Date of Patent: Nov. 19, 1991

[54] SHARPS CONTAINER AND BLANK

[75] Inventors: Bobby L. Boothe; Edward P. Godsey, both of Roanoke, Va.

[73] Assignee: Chesapeake Packaging Company, Richmond, Va.

[21] Appl. No.: 589,959

[22] Filed: Sep. 28, 1990

[51] Int. Cl.5 .............................................. B65D 5/42
[52] U.S. Cl. ................................... 229/151; 206/366; 229/165; 229/178; 229/186; 229/907
[58] Field of Search ............... 206/366, 438; 229/147, 229/151, 152, 153, 165, 178, 186, 907, 8.5

[56] References Cited

U.S. PATENT DOCUMENTS

| | | | |
|---|---|---|---|
| 642,182 | 1/1900 | Webb | 229/147 |
| 1,301,171 | 4/1919 | Richardson | 229/147 |
| 1,603,024 | 10/1926 | Childs | 229/8.5 |
| 2,012,063 | 8/1935 | Unger | 229/8.5 |
| 3,329,146 | 7/1967 | Waldman, Jr. | 128/221 |
| 3,871,545 | 3/1975 | Bereziat | 215/249 |
| 4,121,755 | 10/1978 | Meseke et al. | |
| 4,168,028 | 9/1979 | McCall | 229/147 |
| 4,243,140 | 1/1981 | Thrun | 206/380 |
| 4,254,862 | 3/1981 | Barratt | |
| 4,315,592 | 2/1982 | Smith | |
| 4,373,629 | 2/1983 | Ulin et al. | 206/350 |
| 4,375,849 | 3/1983 | Hanifi | 206/366 |
| 4,454,944 | 6/1984 | Shillington et al. | 206/366 |
| 4,494,652 | 1/1985 | Nelson et al. | 206/366 |
| 4,520,926 | 6/1985 | Nelson | 206/366 |
| 4,552,280 | 11/1985 | Owen et al. | |
| 4,565,311 | 1/1986 | Pugliese et al. | 225/94 |
| 4,576,281 | 3/1986 | Kirksey | 206/370 |
| 4,657,139 | 4/1987 | Hanifi | 220/336 |
| 4,674,676 | 6/1987 | Sandel et al. | 229/142 |
| 4,714,168 | 12/1987 | Johnson et al. | |
| 4,715,498 | 12/1987 | Hanifi | 232/43.1 |
| 4,736,844 | 4/1988 | Scott et al. | 206/370 |
| 4,736,860 | 4/1988 | Bemis | |
| 4,769,026 | 9/1988 | Strung | 604/415 |
| 4,779,728 | 10/1988 | Hanifi et al. | 206/366 |
| 4,801,013 | 1/1989 | Bruno | 206/366 |
| 4,804,090 | 2/1989 | Schuh et al. | 206/366 |
| 4,809,850 | 3/1989 | Laible et al. | 206/366 |
| 4,826,073 | 5/1989 | Bruno | 229/907 |
| 4,828,107 | 5/1989 | Spencer | 206/366 |
| 4,840,272 | 6/1989 | Goldman | 206/365 |
| 4,842,138 | 6/1989 | Sandel et al. | 206/370 |
| 4,848,570 | 7/1989 | Gosciniak | 206/366 |
| 4,867,309 | 9/1989 | Germain | 206/366 |
| 4,886,164 | 12/1989 | Stein et al. | 206/366 |
| 4,886,497 | 12/1989 | Scholl, Jr. | 604/111 |
| 4,905,916 | 3/1990 | Sorwick et al. | 241/23 |
| 4,917,243 | 4/1990 | Abrams et al. | 206/365 |
| 4,922,597 | 5/1990 | Ikeda et al. | 29/240 |
| 4,927,076 | 5/1990 | Simpson | 229/132 |
| 4,927,415 | 5/1990 | Brodsky | 604/164 |
| 4,936,449 | 6/1990 | Conard et al. | 206/366 |
| 4,940,157 | 7/1990 | Inagaki | 220/254 |

Primary Examiner—Gary E. Elkins
Attorney, Agent, or Firm—Joseph G. Seeber

[57] ABSTRACT

A container for receiving and containing items to be disposed of, such as medical waste (used syringes, needles, and the like), is assembled from a blank, and comprises bottom, front, rear, top and end panels. The top panel has a front flap provided with opposing flap tucks which, when the container is assembled, are inserted into spaces between respective end panels and respective minor flaps of the front panel, thereby securing the top panel against inadvertent opening. The top panel also has a syringe-shaped opening which serves as an access to an inner flap of the front panel below so that, when an item to be disposed of is deposited through the opening onto the inner flap, and when a force is exerted on the inner flap from above, the inner flap rotates downward, and the item is deposited in the container. The inner flap is biased to a closed position so that, upon removal of the force, the inner flap rotates back to the closed position.

17 Claims, 3 Drawing Sheets

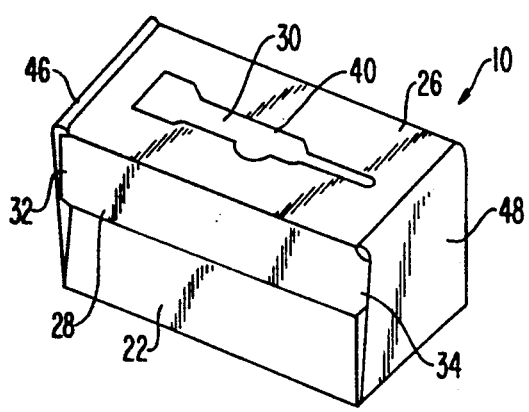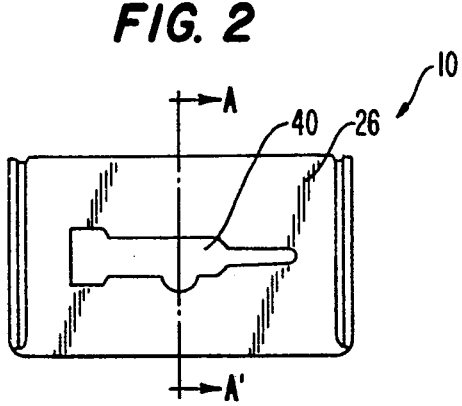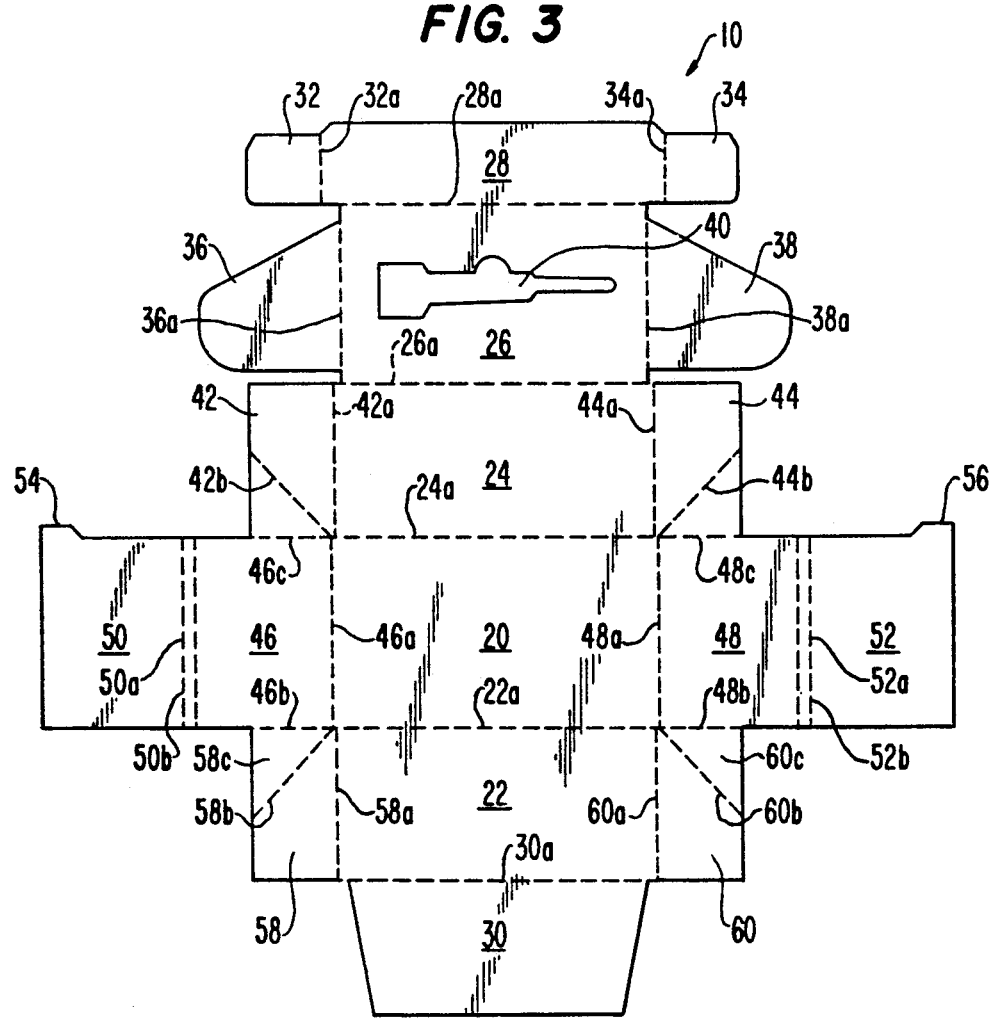

SHARPS CONTAINER AND BLANK

DESCRIPTION

1. Technical Field

The present invention relates to a sharps container and blank, and more particularly to a container formed from a blank for the purpose of receiving and holding medical waste. Such medical waste takes the form of used syringes, needles, and the like. The container is readily assembled from the blank with no additional aids (such as staples, tape, glue, etc.).

2. Background Art

Various types of sharps containers have existed in the prior art, but such containers are burdened by various disadvantages.

Typically, sharps containers of the prior art are fabricated and assembled by the manufacturer, and are shipped in assembled form. This imposes a limit on the number of containers which can be shipped at any given time, and the assembled containers are prone to becoming damaged during shipment. Therefore, it is desirable to develop a sharps container in the form of a blank, the blank being easily shipped to the user, and the user assembling the blank with ease and without the need for additional aids (such as staples, tape, glue, etc.).

Sharps containers of the prior art can also be less than convenient when medical waste is to be inserted into the container. Many containers require the use of two hands, one to open the container, and the other to insert the medical waste. This is an obvious disadvantage to medical personnel who have a need to quickly and efficiently deposit the waste using a single hand. Therefore, it would be desirable to have a sharps container which only requires one hand when medical waste is to be inserted.

In the prior art, sharps containers can be inadvertently opened during use, thus exposing the exterior to the medical waste stored therein. This also is an obvious disadvantage. Therefore, it is desirable to employ a sharps container which, once assembled, is highly resistant to opening, while at the same time being leak resistant, puncture resistant, etc.

The following patents are considered to be typical of the state of the art relative to sharps containers: U.S. Pat. Nos. 4,121,755; 4,315,592; 4,454,944; 4,674,676; 4,714,168; 4,715,498; 4,736,860; 4,779,728; 4,804,090; 4,809,850; 4,842,138; and 4,927,076.

The following patents are considered to be of background interest relative to the present invention: U.S. Pat. Nos. 3,329,146; 3,871,545; 4,243,140; 4,254,862; 4,373,629; 4,375,849; 4,494,652; 4,520,926; 4,552,280; 4,565,311; 4,576,281; 4,657,139; 4,736,844; 4,769,026; 4,801,013; 4,828,107; 4,840,272; 4,848,570; 4,867,309; 4,886,164; 4,886,497; 4,905,916; 4,917,243; 4,922,597; 4,927,415; 4,936,449; and 4,940,157.

DISCLOSURE OF INVENTION

The present invention generally relates to a sharps container and blank, the container being used as a repository for medical waste, that is, for used syringes, needles, and the like. More particularly, the container is produced in the form of a blank which, upon receipt by the user, can be easily assembled by the user without additional aids, such as staples, tape, glue and the like. Preferably, the container is made of a material which is flammable so that the container, once full, can be incinerated along with its contents.

The container is so designed as to facilitate the deposit of needles, syringes and the like by placing such items onto the surface of an inner flap disposed beneath the top panel of the container. The inner flap is connected in hinge-like fashion to the interior of the container, and is accessible through an opening (preferably, a syringe-shaped opening). More specifically, the inner flat is biased to the closed position but, once an item is placed on the inner flap via the opening, the mere push of a finger at a point generally in the center of the opening and flap causes the item to fall into the carton without further human contact. As indicated earlier, once the item is deposited in the container, the inner flap springs back to the closed position, thus sealing the interior of the container.

The container is easily assembled by the user from the blank, and the container is designed so that, once assembled, it will resist opening. This feature is accomplished by the employment of flap tucks attached to a front flap of a top panel of the container, the flap tucks being tucked, during the assembly process, into spaces on either side of the container. In this manner, the container is self-locked, and resists opening during use.

Other features of the container include resistance to leaking, resistance to puncture, and resistance to spilling of the contents of the container once it is assembled.

Therefore, it is a primary object of the present invention to provide a sharps container and blank, the container serving as a repository for medical waste.

It is an additional object of the present invention to provide a sharps container into which medical waste is easily deposited with a minimum amount of effort on the part of the user.

It is an additional object of the present invention to provide a sharps container having an inner flap or entry flap disposed in hinge-like fashion beneath a top panel, and accessible through an opening in the top panel.

It is an additional object of the present invention to provide a sharps container having an entry flap which is manipulated with a minimum amount of effort on the part of the user.

It is an additional object of the present invention to provide a sharps container having an entry flap which is biased to the closed position, so that the container remains closed when items are not being deposited into the container.

It is an additional object of the present invention to provide a sharps container which has a resistance to being opened during use of the container.

It is an additional object of the present invention to provide a sharps container which is leak resistant, puncture resistant, and resistant to being opened or spilling its contents easily.

The above and other objects, and the nature of the invention, will be more clearly understood by reference to the following detailed description, the accompanying drawings, and the appended claims.

BRIEF DESCRIPTION OF DRAWINGS

FIG. 1 is a perspective view of the sharps container of the present invention.

FIG. 2 is a top view of the container of the present invention.

FIG. 3 is a plan view of a blank used to assemble the container of the present invention.

BEST MODE FOR CARRYING OUT THE INVENTION

Figure 4:
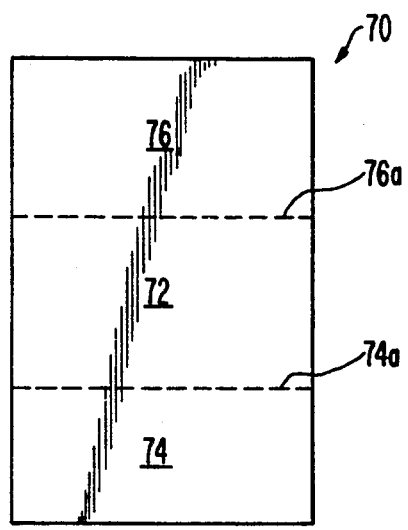
FIG. 4 is a plan view of an insert which is placed in the interior of the container once it is assembled from the blank of FIG. 3.

The invention will now be described in more detail with reference to the accompanying drawings.

FIG. 1 is a perspective view of the container of the present invention, while FIG. 2 is a top view of the container. As seen in FIGS. 1 and 2, the container 10 generally comprises a front panel 22, a top panel 26, a front flap 28 having flap tucks 32 and 34, and side or end panels 46 and 48.

In accordance with one feature of the present invention, the top panel 26 has a syringe-shaped opening or cut out 40 formed therein, and an inner flap 30 is disposed in hinge-like fashion beneath the top panel 26 and opening 40. As mentioned earlier, and as to be described in more detail, this arrangement provides the user with easy access to the interior of the container for the purpose of depositing medical waste therein.

FIG. 3 is a plan view of a blank used to assemble the container of the present invention, while FIG. 4 is a plan view of an insert preferably disposed in the interior of the container once it is assembled.

As seen in FIG. 3, blank 10 comprises the following elements: bottom panel 20, front panel 22, rear panel 24, top panel 26, front flap 28, inner flap 30, and end panels 46 and 48.

Front panel 22 has minor flaps 58 and 60. Rear panel 24 has minor flaps 42 and 44. Top panel 26 has minor flaps 36 and 38. Front flap 28 has flap tucks 32 and 34. Finally, end panels 46 and 48 have end flaps 50 and 52, respectively.

The top panel 26 also has a syringe-shaped cut out 40 formed therein. Folding score 28a separates front flap 28 from top panel 26, while folding scores 32a and 34a separate front flap 28 from flap tucks 32 and 34, respectively. Folding score 26a separates top panel 26 from rear panel 24, while folding scores 36a and 38a separate top panel 26 from minor flaps 36 and 38, respectively. Folding score 24a separates rear panel 24 from bottom panel 20, while folding scores 42a and 44a separate rear panel 24 from minor flaps 42 and 44, respectively, and folding scores 42b and 44b subdivide minor flaps 42 and 44, respectively, in approximately a diagonal fashion. Folding score 22a separates bottom panel 20 from front panel 22, while folding scores 46a and 48a separate bottom panel 20 from end panels 46 and 48, respectively, and dual folding scores 50a, 50b and 52a, 52b separate end panels 46 and 48, respectively, from end flaps 50 and 52, respectively. Folding score 30a separates front panel 22 from inner flap 30, while folding scores 58a and 60a separate front panel 22 from minor flaps 58 and 60, respectively. Finally, folding scores 58b and 60b subdivide minor flaps 58 and 60, respectively, in approximately a diagonal fashion.

FIG. 4 is a plan view of a blank which forms an insert for the container of the present invention. As seen therein, insert 70 comprises bottom insert panel 72, front insert panel 74 and rear insert panel 76. Folding score 74a separates bottom insert panel 72 from front insert panel 74, while folding score 76a separates bottom insert panel 72 from rear insert panel 76.

Preferably, blanks forming the container 10 of FIG. 3 and the insert 70 of FIG. 4 are formed from corrugated material or other similar material. In addition, preferably, the entire surface of container blank 10 is laminated or treated with a water-resistant, leakproof substance.

The assembly of the container 10 will now be described in more detail with reference to the figures mentioned above, and also with reference to FIGS. 5, 6 and 7 which show the container 10 in various stages of assembly.

Figure 5:
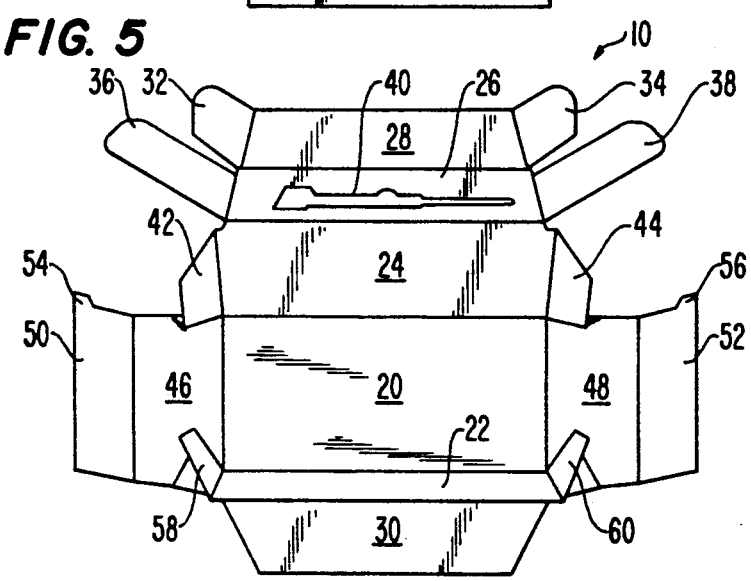
FIG. 5 is a top view of the container as partially assembled from the blank of FIG. 3.

Referring to the plan view of the container 10 shown in FIG. 5, assembly is commenced by folding the container 10 along folding scores 22a and 24a so as to raise front panel 22 and rear panel 24 relative to bottom panel 20. At the same time, minor flaps 42, 44, 58 and 60 are folded along folding scores 42b, 44b, 58b and 60b, respectively, so that minor flaps 42, 44, 58 and 60 take on a convex shape facing upward. End panels 46 and 48 are folded along folding scores 46a and 48a, respectively, so that end panels 46 and 48 also assume an upright position. Finally, in order to lock front panel 22, rear panel 24, end panel 46 and end panel 48 into a fully upright position relative to bottom panel 20, end flaps 50 and 52 are folded, via dual folding scores 50a, 50b and 52a, 52b, respectively, so that end flaps 50 and 52 are suspended over the bottom panel 20, and end flaps 50 and 52 are then pushed down into the container 10 so that they rotate into a rest position next to upright end panels 46 and 48, respectively. It should be noted that end flaps 50 and 52 are forced into their final position so as to overcome the resistance which results from the pressing of tabs 54 and 56 against the interior of rear panel 24. In the latter regard, the final resting position of end flaps 50 and 52 is illustrated in FIG. 6.

Figure 6:
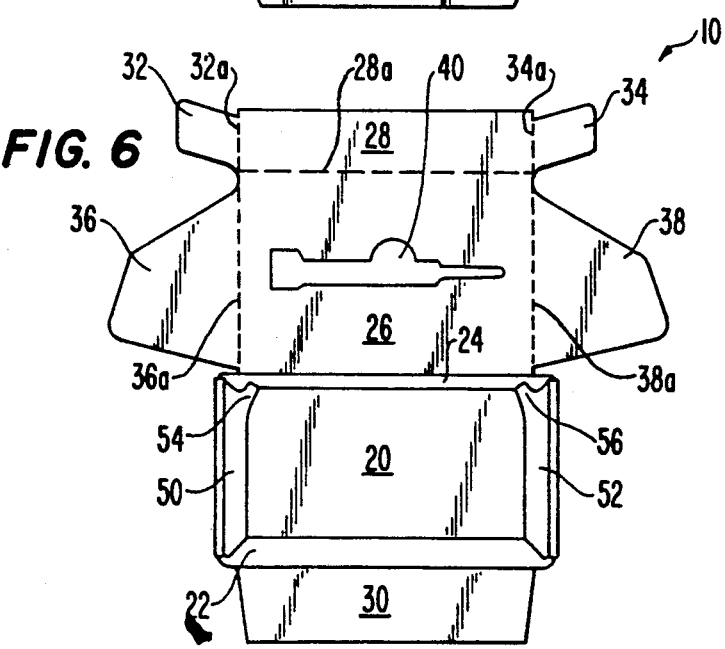
FIG. 6 is a top view of the container in a stage of assembly subsequent to that shown in FIG. 5.
Figure 7:
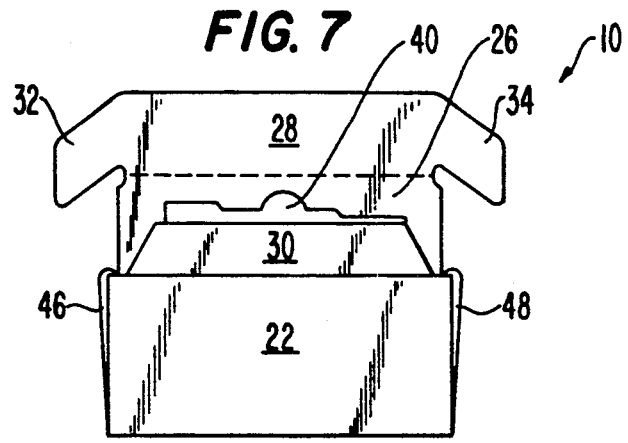
FIG. 7 is a front view of the container in a stage of assembly subsequent to that shown in FIG. 6.

Further referring to FIG. 6, assembly continues by rotating inner flap 30 forward into a position overlying the interior of the container 10 (see FIG. 7). In this regard, it should be noted that, in accordance with the present invention, the folding score 30a between front panel 22 and inner flap 30 establishes a line along which inner flap 30 can be folded, and corrugated material or similar material is used to ensure that the inner flap 30 is upwardly biassed with respect to the interior of the container 10. That is to say, inner flap 30 may be pressed downward into the interior of container 10 to a certain degree but, due to the upward biassing of inner flap 30, release of that pressure results in reverse or upward rotation of the inner flap 30 around folding score 30a.

Further referring to FIG. 7, assembly of the container 10 continues by folding of minor flaps 36 and 38 into a perpendicular position relative to top panel 26, and by folding of flap tucks 32 and 34 into a perpendicular position relative to front flap 28. Top panel 26 and front flap 28 are then rotated forward so that minor flaps 36 and 38 enter the container 10 next to the inner sides of end flaps 50 and 52, respectively. Rotation of top panel 26 continues so that top panel 26 overlies inner flap 30. Finally, as shown in FIG. 1, top panel 26 is locked into final position overlying inner flap 30 by the insertion of flap tucks 32 and 34 into spaces between end panel 46 and folded minor flap 58 in the case of flap tuck 32, and between end panel 48 and folded minor flap 60 in the case of flap tuck 34.

Figure 8:
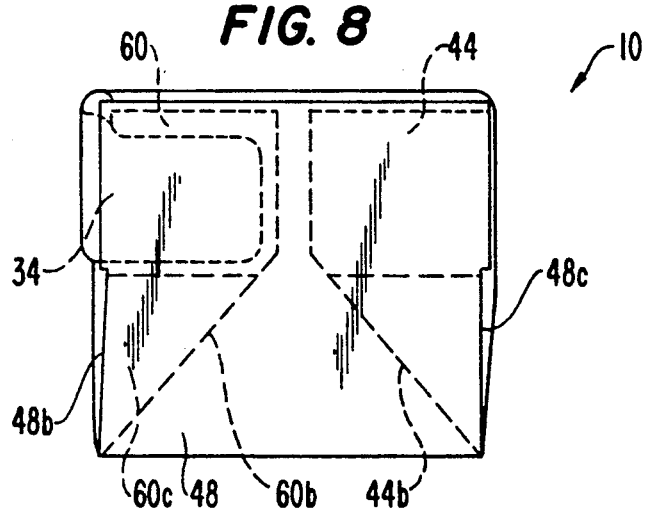
FIG. 8 is a side view of the container illustrating the "flap tuck" feature of the present invention.

The final resting position of flap tuck 34 is illustrated in FIG. 8, which is a side view of the container 10. Flap tuck 34 is shown in dotted line fashion behind end panel 48, with folded portion 60c of minor flap 60 shown in dotted line fashion underlying or lying directly beneath flap tuck 34. In accordance with the "flap tuck" feature of the present invention thus described, once the container 10 is assembled, it is quite resistant to coming open on its own or even being inadvertently opened by the user. In particular, it should be noted that the container 10 can only be opened by determined action by the user in exerting a lateral force to withdraw flap tucks 32 and 34 (FIGS. 1 and 8) from their positions between elements 46 and 58 and between elements 48 and 60, respectively. Thus, inadvertent forces—such as an upward force on the top panel 26—will not result in opening of the container 10 due to blocking action of folded portions 58c and 60c, respectively.

Figure 9:
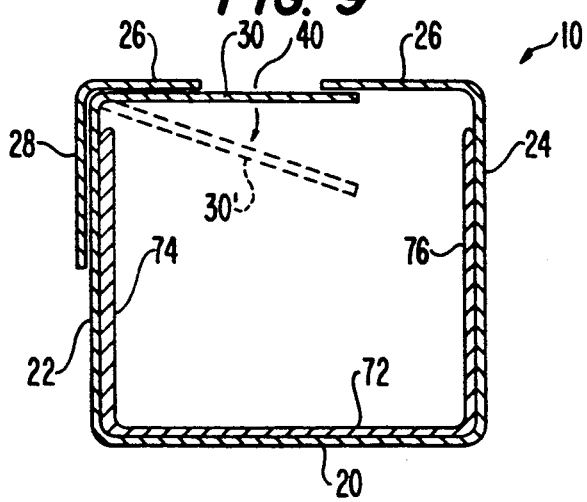
FIG. 9 is a sectional view of the container, taken along line A—A' of FIG. 2, illustrating the deposit of medical waste into the container.

Referring to FIG. 9, which is a sectional view of the container 10 taken along section line A—A' of FIG. 2, assembly is completed by placing the insert 70 into the interior of container 10 so that bottom insert panel 72 rests on bottom panel 20, front insert panel 74 rests beside front panel 22, and rear insert panel 76 rests beside rear panel 24.

Further referring to FIG. 9, the container 10 is used by placing an item to be disposed on that portion of inner flap 30 accessible through the opening 40. The user then presses inner flap 30 so as to rotate it into the position indicated by dotted lines 30', and the item falls into the container 10. Once the user releases pressure on inner flap 30, the inner flap 30 (as a result of its being biased to the upward position, as previously discussed) returns to the upward position indicated by reference numeral 30.

While preferred forms and arrangements have been shown in illustrating the invention, it is to be understood that various changes in detail and arrangement may be made without departing from the spirit and scope of this disclosure.

We claim:

1. A container for receiving and containing items to be disposed of, said container comprising a bottom panel, a front panel, a rear panel, two end panels, a top panel, and a front flap connected to said top panel, said front flap including flap tuck means adapted to be engaged with said two end panels for securing said top panel in a closed condition, wherein said flap tuck means comprises first and second flap tucks disposed on opposite sides of said front flap, said first and second flap tucks being inserted between respective ones of said two end panels and an interior of said container;

said front panel having first and second minor flaps connected to opposite ends of said front panel, said first and second minor flaps being folded and disposed between respective ones of said two end panels and the interior of said container; and wherein at least a folded portion of each of said first and second minor flaps lies directly beneath said first and second flap tucks, respectively, so as to inhibit removal of said first and second flap tucks, whereby the container is resistant to be opened inadvertently.

2. The container of claim 1, further comprising two end flaps, each of said two end flaps being connected to a respective one of said two end panels and being folded so as to form respective interior end walls of said container.

3. The container of claim 2, further comprising first and second additional minor flaps connected to respective opposite ends of said top panel and disposed between respective ones of said two end flaps and the interior of said container.

4. A container for receiving and containing items to be disposed of, said container comprising a bottom panel, a front panel, a rear panel, two end panels, and a top panel, said container further comprising an insert disposed in the interior of said container so as to form a liner for said container, wherein said insert comprises a bottom insert panel disposed on said bottom panel, a front insert panel disposed against said front panel, and a rear insert panel disposed against said rear panel.

5. The container of claim 4, further comprising a front flap connected to said top panel, said front flap including flap tuck means adapted to be engaged with said two end panels for securing said top panel in a closed condition, whereby the container is resistant to being opened inadvertently.

6. A container for receiving and containing items to be disposed of, said container comprising a bottom panel, a front panel, a rear panel, two end panels, and a top panel, wherein said top panel is discontinuous so as to form an opening therein, said container further comprising an inner flap connected to said front panel and extending over an interior of said container and beneath said top panel.

7. The container of claim 6, wherein said inner flap is accessible through said top panel so that an item to be disposed of can be deposited through said opening onto said inner flap.

8. The container of claim 7, wherein said inner flap is hingedly connected to said front panel so that a force exerted on said inner flap from above causes said inner flap to move inwardly and to deposit any item placed on said inner flap into said container.

9. The container of claim 8, wherein said inner flap is biased toward said top panel so that, when force is not exerted on said inner flap, said inner flap remains in a closed position against said top panel.

10. The container of claim 6, wherein said inner flap is biased toward said top panel so that, when force is not exerted on said inner flap, said inner flap remains in a closed position against said top panel.

11. The container of claim 6, further comprising a front flap connected to said top panel, said front flap including flap tuck means adapted to be engaged with said two end panels for securing said top panel in a closed condition, whereby the container is resistant to being opened inadvertently.

12. A container for receiving and containing items to be disposed of, said container comprising a bottom panel, a front panel, a rear panel, two end panels, and a top panel, wherein said top panel is discontinuous so as to form an opening therein, said container further comprising an inner flap connected to said front panel and extending over an interior of said container and beneath said top panel;

wherein said inner flap is accessible through said top panel so that an item to be disposed of can be deposited through said opening onto said inner flap; and wherein said inner flap is unbroken and continuous so that any item deposited through said opening rests on said inner flap, said inner flap being hingedly connected to said front panel so that a force exerted on said inner flap from above causes said inner flap to move inwardly and to deposit any item placed on said inner flap into said container.

13. The container of claim 12, wherein said inner flap is biased toward said top panel so that, when force is not exerted on said inner flap, said inner flap remains in a closed position against said top panel.

14. A blank for forming a container for receiving and containing items to be disposed of, said blank having a plurality of score lines to form, when said blank is assembled into said container, a bottom panel, a front panel, a rear panel, two end panels, a top panel, and a front flap connected to said top panel, said front flap including flap tuck means adapted to be engaged with said two end panels for securing said top panel in a closed condition, wherein said flap tuck means comprises first and second flap tucks disposed on opposite sides of said front flap, said first and second flap tucks being inserted between respective ones of said two end panels and an interior of said container;

said front panel having first and second minor flaps connected to opposite ends of said front panel, said first and second minor flaps being folded and disposed between respective ones of said two end panels and the interior of said container; and wherein at least a folded portion of each of said first and second minor flaps lies directly beneath said first and second flap tucks, respectively, so as to inhibit removal of said first and second flap tucks, whereby the container is resistant to being opened inadvertently.

15. A blank for forming a container for receiving and containing items to be disposed of, said blank having a plurality of score lines to form, when said blank is assembled into said container, a bottom panel, a front panel, a rear panel, two end panels, and a top panel, said container further comprising an insert disposed in the interior of said container so as to form a liner for said container, wherein said insert comprises a bottom insert panel disposed on said bottom panel, a front insert panel disposed against said front panel, and a rear insert panel disposed against said rear panel.

16. A blank for forming a container for receiving and containing items to be disposed of, said blank having a plurality of score lines to form, when said blank is assembled into said container, a bottom panel, a front panel, a rear panel, two end panels, and a top panel, wherein said top panel is discontinuous so as to form an opening therein, said blank having further score line to form, when said blank is assembled into said container, an inner flap connected to said front panel and extending over an interior of said container and beneath said top panel;

wherein said inner flap is accessible through said top panel so that an item to be disposed of can be deposited through said opening onto said inner flap.

17. A blank for forming a container for receiving and containing items to be disposed of, said blank having a plurality of score lines to form, when said blank is assembled into said container, a bottom panel, a front panel, a rear panel, two end panels, and a top panel, wherein said top panel is discontinuous so as to form an opening therein, said container further comprising an inner flap connected to said front panel and extending over an interior of said container and beneath said top panel;

wherein said inner flap is accessible through said top panel so that an item to be disposed of can be deposited through said opening onto said inner flap; and wherein said inner flap is unbroken and continuous so that any item deposited through said opening rests on said inner flap, said inner flap being hingedly connected to said front panel so that a force exerted on said inner flap from above causes said inner flap to move inwardly and to deposit any item placed on said inner flap into said container.

* * * * *